US010172696B2

United States Patent
Alqarawi

(10) Patent No.: US 10,172,696 B2
(45) Date of Patent: Jan. 8, 2019

(54) METHOD FOR PRODUCING A CERAMIC FIXED PARTIAL DENTURE

(71) Applicant: Firas Khalid Alqarawi, Medford, MA (US)

(72) Inventor: Firas Khalid Alqarawi, Medford, MA (US)

(*) Notice: Subject to any disclaimer, the term of this patent is extended or adjusted under 35 U.S.C. 154(b) by 191 days.

(21) Appl. No.: 15/182,646

(22) Filed: Jun. 15, 2016

(65) Prior Publication Data
US 2017/0360536 A1 Dec. 21, 2017

(51) Int. Cl.
A61C 13/083 (2006.01)
A61C 13/00 (2006.01)
A61C 13/225 (2006.01)

(52) U.S. Cl.
CPC ........ *A61C 13/083* (2013.01); *A61C 13/0016* (2013.01); *A61C 13/0018* (2013.01); *A61C 13/0022* (2013.01); *A61C 13/2255* (2013.01); *C04B 2235/3244* (2013.01); *C04B 2235/3246* (2013.01)

(58) Field of Classification Search
CPC .............. A61C 13/083; A61C 13/0016; A61C 13/0018
See application file for complete search history.

(56) References Cited

U.S. PATENT DOCUMENTS

| 5,080,589 | A | 1/1992 | Odén et al. |
| 6,238,601 | B1 | 5/2001 | Salomonson et al. |
| 6,371,762 | B1* | 4/2002 | Foser ................. A61C 13/0003 433/180 |
| 8,592,330 | B2 | 11/2013 | Johannes et al. |
| 2004/0197738 | A1* | 10/2004 | Ban ........................ A61C 13/26 433/202.1 |
| 2017/0128174 | A1* | 5/2017 | Mayr ...................... C03C 3/097 |

OTHER PUBLICATIONS

"Dental Wings Laser Milling," Inside Dentistry vol. 11, Issue 4, Apr. 2015. https://www.aegisdentalnetwork.com/id/2015/04/dental-wings-laser-milling.*
"Prosthetics", Hyderabad Dental Hospital >> Prosthodontics, http://hyderabaddental.co.in/prosthodontics/, Feb. 6, 2015, 5 pages.

* cited by examiner

*Primary Examiner* — Jacob T Minskey
*Assistant Examiner* — Melody Tsui
(74) *Attorney, Agent, or Firm* — Oblon, McClelland, Maier & Neustadt, L.L.P.

(57) ABSTRACT

A method for making ceramic fixed partial dentures comprising separating the as-sintered partial denture structure, rejoining the retainers and pontic with glass, which forms a strong joint between the retainers and pontic after sintering. This method may produce ceramic long-span fixed partial dentures with a better fit.

18 Claims, 12 Drawing Sheets

METHOD FOR PRODUCING A CERAMIC FIXED PARTIAL DENTURE

GRANT OF NON-EXCLUSIVE RIGHT

This application was prepared with financial support from the Saudi Arabian Cultural Mission, and in consideration therefore the present inventor has granted The Kingdom of Saudi Arabia a non-exclusive right to practice the present invention.

BACKGROUND OF THE INVENTION

Field of the Invention

This disclosure relates to the fabrication of ceramic fixed partial dentures to replace missing teeth in the anterior and posterior areas of the mouth.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In modern dentistry, metal frameworks are used as a substructure for porcelain veneer fixed partial denture because the metal substructures increased the fracture resistance of the fixed partial dentures. However, the use of metals in such restorations has problems such as dark margins and metal-related allergies. For example, a dark margin at the cervical margin makes the gums look darker and the patients are often displeased with the aesthetics of the final restoration (Emil Hawary, Journal of the California Dental Association, 2014, 319-324—incorporated herein by reference in its entirety). Therefore, the demand for more natural-looking restorations, such as ceramic restorations, and prostheses has increased. Ceramic frameworks, however, have shown more vertical gaps compared to metal frameworks: the cervical margin of the ceramic frameworks is about 189.6±71.8 µm, while that of metal-ceramic fixed partial dentures is about 118.6±31.5 µm (Fabian Wettstein et al., European Journal of Oral Sciences, 2008, 272-279—incorporated herein by reference in its entirety). More importantly, the longer the span of the ceramic framework, the higher the chances of a poor fit, and this challenge has resulted in a preference for metal-ceramic fixed partial dentures for long-span fixed partial dentures.

In view of the foregoing, one objective of the present disclosure is to provide a method for producing ceramic long-span fixed partial dentures with a better fit.

SUMMARY OF THE DISCLOSURE

The foregoing description is intended to provide a general introduction and summary of the present disclosure and is not intended to be limiting in its disclosure unless otherwise explicitly stated. The presently preferred embodiments, together with further advantages, will be best understood by reference to the following detailed description taken in conjunction with the accompanying drawings.

A first aspect of the disclosure relates to a method for forming a fixed partial denture, comprising: (i) milling a porous ceramic block into a shape of a series of teeth thereby forming a pre-sintered framework structure comprising a plurality of retainers and a pontic located between and connected to adjacent retainers via a connector, (ii) sintering the pre-sintered framework structure thereby forming an initial sintered framework structure, (iii) separating the initial sintered framework structure at the connector thereby providing a plurality of sintered retainers and a sintered pontic, (iv) seating each sintered retainer and aligning the sintered pontic on a respective tooth abutment within a patient's mouth or on a dental model so as to provide an accurate fit, and (v) rejoining each sintered retainer to the sintered pontic thereby forming a final framework structure and sintering to form the fixed partial denture.

In one embodiment, the porous ceramic block comprises porous pre-sintered zirconia.

In one embodiment, the porous ceramic block further comprises yttrium oxide.

In one embodiment, at least one of the pre-sintered framework structure and the final framework structure is sintered in a pressure ranging from 1-50 mbar.

In one embodiment, at least one of the pre-sintered framework structure and the final framework structure is sintered at a temperature ranging from 900° C. to 1500° C.

In one embodiment, at least one of the pre-sintered framework structure and the final framework structure is sintered at a temperature ranging from 1000° C. to 1200° C.

In one embodiment, at least one of the pre-sintered framework structure and the final framework structure is sintered for a period ranging from 1-60 minutes.

In one embodiment, at least one of the pre-sintered framework structure and the final framework structure is sintered for a period ranging from 5-10 minutes.

In one embodiment, the initial sintered framework structure is separated by ultrasonic vibration-assisted machining, laser-assisted machining, or thermal-assisted machining.

In one embodiment, the initial sintered framework structure is separated by laser-assisted machining.

In one embodiment, the initial sintered framework structure is separated by ultrasonic vibration-assisted machining, laser-assisted machining, or thermal-assisted machining, and the method further comprises separating the initial sintered framework structure with a machining tool heated to a temperature up to 500° C.

In one embodiment, the accurate fit is provided by seating each sintered retainer and aligning the sintered pontic on the respective tooth abutment within the patient's mouth.

In one embodiment, the accurate fit is provided by seating each sintered retainer and aligning the sintered pontic on the respective tooth abutment of the dental model.

In one embodiment, each sintered retainer is rejoined to the sintered pontic by applying a glass therebetween.

In one embodiment, the glass is in the form of a paste.

In one embodiment, the fixed partial denture comprises: (i) at least 90% $ZrO_2$ by weight, (ii) at least 3% $Y_2O_3$ by weight, (iii) at least 1% $HfO_2$ by weight, (iv) no more than 0.1% $Al_2O_3$ by weight, (v) no more than 0.1% $SiO_2$ by weight, and (vi) no more than 0.1% $Na_2O$ by weight of the fixed partial denture.

A second aspect of the disclosure relates to a fixed partial denture, comprising: (i) at least 90% $ZrO_2$ by weight, (ii) at least 3% $Y_2O_3$ by weight, (iii) at least 1% $HfO_2$ by weight, (iv) no more than 0.1% $Al_2O_3$ by weight, (v) no more than 0.1% $SiO_2$ by weight, and (vi) no more than 0.1% $Na_2O$ by weight of the fixed partial denture, which does not have a porcelain veneer and comprises a plurality of retainers and a pontic located between and connected to adjacent retainers via a connector.

In one embodiment, the fixed partial denture comprises: (i) 91-94% $ZrO_2$ by weight, (ii) 4-6% $Y_2O_3$ by weight, (iii) 2-4% $HfO_2$ by weight, (iv) no more than 0.1% $Al_2O_3$ by weight, (v) no more than 0.1% $SiO_2$ by weight, and (vi) no more than 0.1% $Na_2O$ by weight of the fixed partial denture.

In one embodiment, the fixed partial denture has a failure load in a range of 200-700 N.

DETAILED DESCRIPTION OF THE DISCLOSURE

Figure 1:
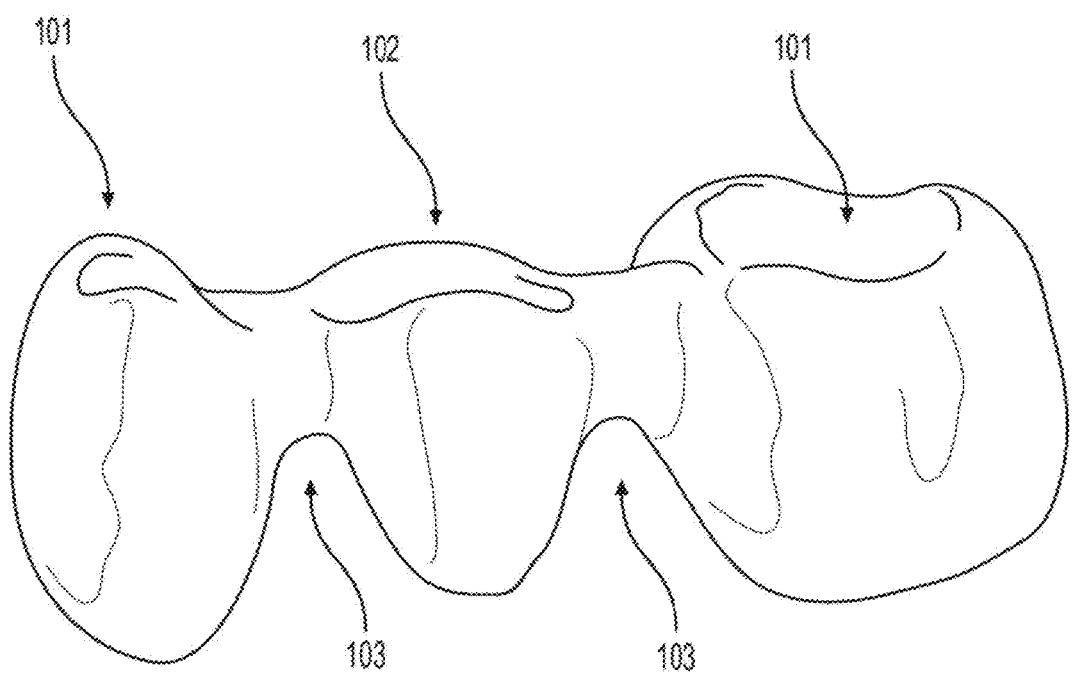
FIG. 1 shows an embodiment of the fixed partial denture.

Embodiments of the present disclosure will now be described more fully hereinafter with reference to the accompanying drawings, in which some, but not all embodiments of the disclosure are shown.

Within the description of this disclosure, where a numerical limit or range is stated, the endpoints are included unless stated otherwise. Also, all values and subranges within a numerical limit or range are specifically included as if explicitly written out. As used herein, the words "a" and "an" and the like carry the meaning of "one or more".

Ceramic dental frameworks may shrink upon sintering and hence not fit well on the master cast. The disclosed method would help repair long-span fixed partial dentures or frameworks for fixed partial dentures through sectioning and fusing the dentures/frameworks. More importantly, the method may be used to fabricate new ceramic long-span fixed partial dentures with a good fit. As used herein, the term "long-span" refers to a fixed partial denture which replaces two or more teeth and takes support from more than one abutment on either side. Dental clinics, laboratories, and patients will benefit because the disclosed method can produce metal-free long-span fixed partial dentures which are aesthetically pleasing and can withstand biting and chewing forces.

The milling of the porous ceramic block may be accomplished with methods and parameters known to those skilled in the art. Non-limiting examples of the method include CAD/CAM (computer-aided design and computer-aided manufacturing) milling and copying milling. Preferably, CAD/CAM milling is used and the CAD/CAM machine typically includes a 3D scanning device, a milling machine and a sinter furnace, all of which are controlled by appropriate computer software. The workflow starts with the dentist or clinician taking an impression from the patient and sending this impression to a dental technician. The dental technician builds a plaster model based on the impression and scans this model with the 3D scanner. Alternatively, the method may involve taking a 3D image of a patient's dentition directly with a 3D scanner (e.g. an iTero® intraoral scanner) without taking a plaster-based model. Based on the scanned data, the dental technician designs a new dental restoration 3D model. This 3D model is the basis for the CAD/CAM process and is customized for each patient. The dental restoration 3D model may be scaled accordingly to take into account the predicted shrinkage that occurs during the sintering phase. Exemplary CAD/CAM systems include the CEREC (Chairside Economical Restoration of Esthetic Ceramics) System manufactured by Siemens Dental Products Division and the PROCERA All-Ceramic system of Nobel Biocare AD. The milling may be dry or wet. In a preferred embodiment, wet milling uses distilled water as a coolant for the tools and material which is being milled (e.g. the porous ceramic block). The method may involve milling with a rotational speed from 11,500 rpm to 40,000 rpm, preferably 20,000 rpm to 40,000 rpm, more preferably 25,000 rpm to 30,000 rpm. A feeding rate may range from 400 mm/min to 2,400 mm/min, preferably 500 mm/min to 2,000 mm/min, more preferably 900 mm/min to 1,500 mm/min. An axial step width may range from 0.01 mm to 1 mm, preferably 0.01 mm to 0.8 mm, more preferably 0.01 mm to 0.3 mm. A radial step width may range from 0.01 mm to 1 mm, preferably 0.01 mm to 0.8 mm, more preferably 0.01 mm to 0.3 mm. The pre-sintered initial framework may be abrasively blasted with alumina particles or sand. In a preferred embodiment, the pre-sintered initial framework is abrasively blasted with alumina particles with diameters ranging from 1-250 μm, preferably 10-100 μm, more preferably 25-50 μm. The pre-sintered initial framework may be mounted on a sample holder at a distance of 5-30 mm, preferably 5-20 mm, more preferably 7-13 mm from the tip of a sandblaster unit. A diameter of the nozzle may range from 2-20 mm, preferably 2-10 mm, more preferably 3-7 mm. An air pressure used to eject alumina particles may range from 2-7 bar, preferably 2-5 bar, more preferably 3.5-4.5 bar.

Non-limiting examples of ceramic include silica, alumina, and zirconia. Preferably, the porous ceramic block comprises porous pre-sintered zirconia. In one embodiment, the porous ceramic block further comprises a stabilizing agent such as calcium oxide, magnesium oxide, cerium oxide, yttrium oxide, and mixtures thereof. Preferably, the porous ceramic block comprises yttrium oxide. In a preferred embodiment, a porous ceramic block of VITA In-Ceram® YZ is used. In other embodiments, the porous ceramic block may comprise fillers such as leucite, lithium disilicate, and glass.

The pre-sintered initial framework is not limited to a fixed shape and may have a shape of a series of teeth, which is exemplified in FIG. 1. An example of the pre-sintered initial framework comprises two retainers (also known as artificial tooth crowns) 101 connected to a central pontic 102 (a substitute for a lost tooth) via a connector 103. In another embodiment, there is at least two pontics in a series and at least one retainer on both sides of the series of pontics. Preferably, there are two pontics. The retainer may comprise an internal cavity which is sized to fit on an abutment, which can be a part of an implant, a root canal pin, or a part of a bridge. Non-limiting examples of the series of teeth may include: (i) the canine, the first premolar, and the second premolar, with the first premolar as the pontic, and the canine and the second premolar as the retainers, (ii) the canine, the first premolar, the second premolar, and the first molar, with the first and second premolar as the pontics, and the canine and the first molar as the retainers, and (iii) the lateral incisor, the canine, and the first premolar, with the canine as the pontic, and the lateral incisor and the first premolar as the retainers.

The pre-sintered framework structure, the final sintered framework structure, or both may be sintered in vacuum, under atmospheric pressure, or under increased pressure. Preferably, the structure is sintered in vacuum. The pressure may range from 1-400 mbar, preferably 1-200 mbar, more preferably 1-50 mbar. The structure may be heated at a rate ranging from 50-200° C./min, preferably 70-130° C./min, more preferably 70-90° C./min to the desired temperature. In other embodiments, the heating rate ranges from 5-45° C./min, preferably 10-30° C./min, more preferably 15-20° C./min. The desired temperature ranges from 900° C. to 1500° C., preferably 1000° C. to 1300° C., more preferably 1000° C. to 1200° C., and may be held for a duration ranging from 1-60 minutes, preferably 1-30 minutes, more preferably 5-10 minutes. In other embodiments, the desired temperature ranges from 1500° C. to 1900° C., preferably 1500° C. to 1700° C., more preferably 1500° C. to 1600° C. The desired temperature may be reached with at least one heating step. In a preferred embodiment, two heating steps are involved. For example, a first heating step heats the structure to a temperature ranging from 400° C. to 700° C., preferably 500° C. to 650° C., more preferably 580° C. to 610° C., and the temperature is held for a duration ranging from 1-10 minutes, preferably 2-6 minutes, more preferably 4-6 minutes. Subsequently, a second heating step heats the structure to the aforementioned desired temperature. The final framework structure may preferably be sintered in the homogeneous temperature zone of the furnace where the temperature gradients may be practically absent to further prevent distortion and uneven shrinkage in the fixed partial denture.

The separation of initial sintered framework may be accomplished with methods, such as ultrasonic vibration-assisted machining, thermal-assisted machining, and laser-assisted machining, known to those skilled in the art. Preferably, laser-assisted machining is used. A gas or solid state laser may be used. In gas lasers, an electric current is liberated from a gas to generate a consistent light. Exemplary gases include, but are not limited to, helium, neon, argon, carbon dioxide, and mixtures thereof. Preferably a solid state laser is used. Non-limiting examples of a crystal for the solid state laser include ruby, yttrium aluminum garnet (YAG), neodymium-doped yttrium aluminum garnet (Nd:YAG), and neodymium-doped gain media (Nd:glass) made of either silicate or phosphate materials. Preferably, Nd:YAG crystal is used. The laser power ranges from 300-1000 W, preferably 300-600 W, more preferably 300-400 W. The laser beam is oriented normal to the longitudinal axis of the initial sintered framework structure. The sample (e.g. the initial sintered framework structure) may be fed into the path of the laser beam at a feed rate range from 100-1000 mm/min, preferably 200-700 mm/min, more preferably 200-400 mm/min. After the sample has been heated by the laser, the sample is then separated with a cutting or machining tool. The cutting speed may range from 0.5-10 m/s, preferably 0.5-5 m/s, more preferably 0.5-2 m/s. In one embodiment, thermal-assisted machining, which comprises a machining tool, is used to separate the initial sintered framework structure. The machining tool may comprise a diamond bur shaped like a cylinder, flame, or a cone. Preferably, the diamond bur has a cone shape and a pointed nose which is preferred for cutting ceramics. A grit size of the diamond bur may range from 4-150 µm, preferably 20-100, more preferably 30-50 µm. A diameter, measured at the widest portion of the diamond bur, ranges from 0.5-3 µm, preferably 0.5-2 µm, more preferably 1-2 µm. In one embodiment, the thermal-assisted machining comprises heating the machining tool to a temperature up to 500° C., preferably in a range of 200-500° C., more preferably 400-500° C. to facilitate the separation of the initial sintered framework (Toru Kizaki, Kanako Harada, Mamoru Mitsuishi, CIRP Annals Manufacturing Technology, 2014, 105-108—incorporated herein by reference in its entirety). The machining tool may be heated by a gas torch or induction heating. In a preferred embodiment, the machining tool is heated by induction heating.

An adhesive is applied between the sintered retainers and the sintered pontic to rejoin the sintered components. A brush may preferably be used to apply the adhesive on the cut surfaces of the sintered pontic and the sintered retainers. Non-limiting examples of the adhesive include adhesive resin cement, glass, colloidal zirconia, and mullite zirconia. Glass may comprise alumina, zirconia, boron oxide, and mixtures thereof. The glass may comprise 20-99 wt % of alumina, preferably 20-70 wt %, preferably 30-70 wt %, and 1-50 wt % of zirconia, preferably 20-40 wt %, more preferably 25-35 wt % of the weight of the glass. In another embodiment, the glass comprises up to 30 wt % of boron oxide, preferably up to 20 wt %, more preferably up to 10 wt % of the weight of the glass. The glass may be used in the form of a powder or a paste. The glass powder comprises glass particles with diameters ranging from 0.5-100 µm, preferably 0.5-20 µm, more preferably 0.5-10 µm. In a preferred embodiment, a glass paste is used. The glass paste may be formed by mixing glass powder with less volatile solvents such as water, polyethylene glycol, and ethylene glycol. The glass paste may comprise at least 80% of glass powder by weight, relative to the total weight of the glass paste, preferably at least 85% by weight, more preferably at least 90% by weight. The amount of glass paste applied between the sintered retainers and the sintered pontic may range from 1-50 mg, preferably 1-20 mg, more preferably 1-10 mg, which may correlate to 0.1-5 wt %, preferably 0.1-2 wt %, more preferably 0.1-1 wt % relative to a total weight of the sintered retainers and the sintered pontic.

The accurate fit of each sintered retainer and an alignment of the sintered pontic may be determined by placing each sintered retainer and the sintered pontic into a patient's mouth or onto a dental model. For example, the accurate fit of the sintered retainer may be found by fitting the sintered retainer on the abutment on the dental model. The sintered pontic may be aligned with respect to the sintered retainers to correct a discrepancy in an angle or a gap as found in the initial sintered framework. For example, an aligned sintered pontic may have a cervical margin ranging from 50-150 µm, preferably 50-100 µm, preferably 50-80 µm. As soon as the fit has been found, it is favorable and beneficial to reinforce the structure with a suitable clamp. In order to obtain an acceptable fit, the sintered retainers and the sintered pontic should remain in their mutual positions during the whole rejoining process. For example, by performing the rejoining process with the sintered retainers and the sintered pontic placed on a refractory die e.g. a refractory replica of the base model of the situation in the mouth, the position of the sintered retainers and the sintered pontic could be locked during the sintering process and thus obtain a good fit.

After sintering, the cooling of the fixed partial denture may be controlled and/or accelerated with a pre-set program. In a preferred embodiment, the fixed partial denture is cooled down at a rate ranging from 1-20° C./s, preferably 1-10° C./s, more preferably 5-10° C./s by a flow of nitrogen gas. During the cooling process, the glass would solidify thereby forming a high strength joint joining the sintered retainers to the sintered pontic.

The fixed partial denture comprises: (i) at least 90% $ZrO_2$ by weight, preferably 90-98%, more preferably 91-94%; (ii) at least 3% $Y_2O_3$ by weight, preferably 3-10%, more preferably 4-6%; (iii) at least 1% $HfO_2$ by weight, preferably 1-5%, more preferably 2-4%; (iv) no more than 0.1% $Al_2O_3$ by weight, preferably no more than 0.07%, more preferably no more than 0.04%; (v) no more than 0.1% $SiO_2$ by weight, preferably no more than 0.07%, more preferably no more than 0.04%; and (vi) no more than 0.1% $Na_2O$ by weight, preferably no more than 0.07%, more preferably no more than 0.04%, of the fixed partial denture.

The fixed partial denture is not limited to a fixed shape. Like the pre-sintered initial framework structure, the fixed partial denture may have a shape of a series of teeth, which comprises two retainers connected to a central pontic (a substitute for a lost tooth) via a connector. The aforementioned description of the pre-sintered initial framework structure is also relevant to the fixed partial denture. In one embodiment, the fixed partial denture does not have a porcelain veneer which provides an aesthetic appearance. In one embodiment, the fixed partial denture has a composite veneer. In an alternative embodiment, the fixed partial denture does not have a composite veneer. In a preferred embodiment, the fixed partial denture does not contain a metal support. Exemplary metals include chrome-cobalt alloy and stainless steel. In another embodiment, the fixed partial denture does not have the glass adhesive covering at least 50% of the surface area of the denture, preferably at least 20%, more preferably at least 5%.

The fixed partial denture may have a failure load in a range of 200-700 N, preferably 400-700 N, more preferably 400-600 N. In a preferred embodiment, when VITA In-Ceram ZR is used to bond the sintered pontic to the sintered retainers and the final framework structure is heated at a rate ranging from 75-85° C./min to 1150-1250° C., the fixed partial denture may have a failure load in a range of 400-500 N, which is comparable to the maximum occlusal loads or biting forces present intra-orally.

The present embodiments are being described with reference to specific example embodiments and are included to illustrate but not limit the scope of the invention.

Example 1 Materials and Methods 174 specimens were used in this study and they were divided according to the adhesive used:
Group R, RelyX Unicem 2 Clicker (control);
Group M, Multilink Automix;
Group V, VITA VM9;
Group G, VITA In-Ceram ZR (infusion glass);
Group AG, infusion glass 30% and $Al_2O_3$ 70%;
Group F, frit (infusion glass 90% and $B_2O_3$ 10%);
Group C, colloidal zirconia; and
Group MZ, mullite zirconia.

Figure 2:
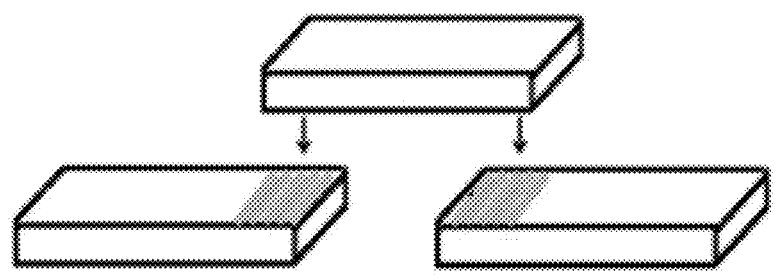
FIG. 2 is an expanded view of a specimen. The shaded area is where the adhesive is applied and the center bar joins the other two bars.
Figure 3:
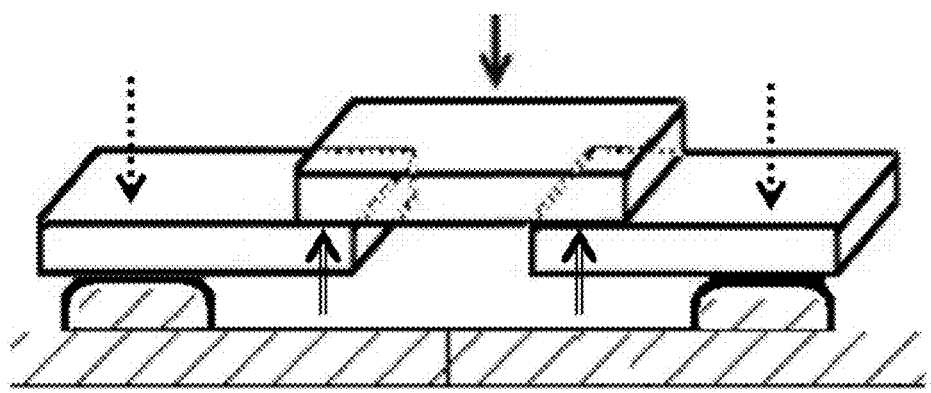
FIG. 3 shows a specimen arranged in geometry A.

A specimen consisted of three $ZrO_2$ bars bonded or fused together. The adhesives used to join the bars covered a surface area of 3×4 $mm^2$. This surface area was determined with a line marked with a pencil placed 3 mm from the edges of the left and right bars and 3 mm from both edges of the middle bar (FIG. 2). Referring to FIG. 3, the solid arrow points to the pontic, the dotted arrows point to the retainers, and the double arrows point to where the sectioning would take place and the sections rejoined using the adhesives. These bars were fabricated from VITA IN-CERAM YZ blocks (20/15, for inLab). The blocks were sectioned using a Buehler Isomet 2000 precision saw with a diamond disc (5-inch diameter, 0.5-mm thick), using a load of 500 g at 2500 rpm, and a constant flow of water to ensure cooling and lubrication. The dimensions of the bars, taken with a digital micrometer (Mitutoyo Absolute 500 series) with an accuracy of 0.01 mm, were: 2 mm thick (T), 5 mm wide (W), and 12 mm long (L). Irregularities of each bar were removed prior to sintering by using a Buehler EcoMet® 250 Grinder-Polisher with an ultra-prep diamond grinding disc (Buehler 45-ram, Buehler Ltd) at a speed of 40 rpm.

The bars were then sintered in a programmable furnace, VITA Zyrcomat T, resulting in shrinkage of around 22%. 20 $ZrO_2$ bars were placed in a ceramic firing tray. The parameters were: a rising time of 90 minutes, a heating rate of 17° C./min with an end temperature of 1530° C. held for 2 hours. The total time from the sintering process until the samples cooled to room temperature, was nearly 8 hours. The sintered bars were measured with the same digital micrometer to record the dimensions of each bar: T: 1.5±0.1×W: 4±0.1× L: 10±0.1 mm. A weighing scale, Mettler PM 480 Delta Range, was used to weigh the bars before they are joined.

For some specimens, the bars were abrasively blasted with 25-50 μm $Al_2O_3$ particles.

Example 2 Bonding Procedures

RelyX Unicem 2 clicker, a dual-curing, self-adhesive resin cement, was used to prepare the Group R specimens. Group R was divided into two subgroups: the first group (RA) was as-sintered with no surface treatment and the second group (RSb) was abrasively blasted. The cement consists of a base and a catalyst. Both components are in the form of a paste and were simultaneously extruded onto a mixing pad, and mixed for 20 seconds with a plastic spatula. The mixing ratio, based on volume, was 1:1. A customized fixture was made to hold the bars in place for curing. A weight of 100 g was placed while the cement was being cured by light. The initial curing time was 1 to 2 seconds. After which, excess cement was removed, then each surface was cured for an additional 20 seconds.

In group Ram, Monobond was used with RelyX Unicem 2 clicker to determine the effect of Monobond on another self-adhesive resin cement. The binding and curing procedures were similar to those of group R.

Figure 4:
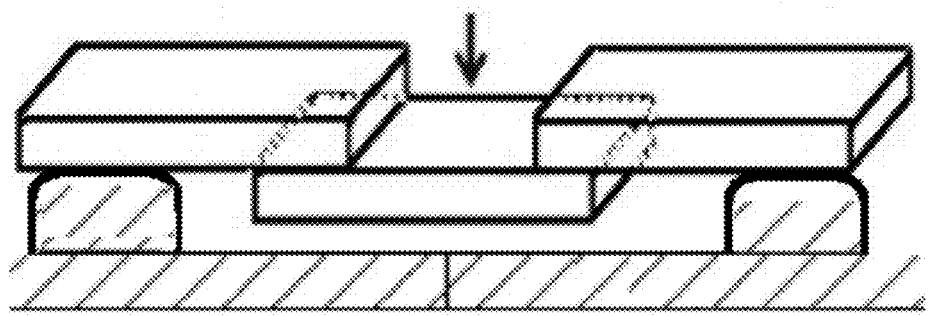
FIG. 4 shows a specimen arranged in geometry B.

Group R specimens were tested in two different geometries, geometry A (FIG. 3) and geometry B (FIG. 4). Specimens in geometry A were labelled R-GA and had the lowest mean failure load. Therefore, geometry A was chosen for the specimens in other groups.

Multilink Automix, a self-curing luting resin composite, was used to prepare the specimens for Group M. The composite consists of a base and a catalyst, both in the form of a paste. The two components were mixed in the tip of an automix syringe while they were dispensed at a mix ratio of 1:1. This group had two subgroups: the first group (MA) was as-sintered which had no surface treatment and the second group (MSb) consisted of abrasively blasted bars. Both subgroups were used in two different experiments: one consisted of coating the bars with Monobond (MA-m) while the other had no Monobond coating (MA-nm). The bonding process was done with the same customized fixture and weight that was used for group R, however the curing time was 2 to 4 seconds for each of the four surfaces of the bonded area for both sides of the specimen, and a final curing of 20 seconds for each of the bonded joints.

Example 3 Sintering Procedures

Groups V, G, F, AG, C and MZ, consisted of materials that were sintered in a Vacumat 200 furnace (VITA Zahnfabrik). Each of these groups was used in different experiments with various sintering parameters: some with surface treatments (e.g. abrasive blasting) and others that had a weight on the specimens while being sintered. Materials used to bond the $ZrO_2$ bars were mixed with deionized water using a small plastic spatula, and then the mix was placed on the two bars at the areas that are assumed to fuse with the third bar to be connected together. The specimens were then placed on a firing tray and sintered.

Group V specimens used VITA VM9 and were divided into 5 subgroups (V1-V5), where the specimens were sintered at different end temperatures for different durations at the end temperature and in vacuum. Group V1 specimens were sintered to 950° C., held for 5 minutes with 10 minutes of vacuum. Group V2 specimens were sintered to 980° C., held for 1 minute with 7 minutes of vacuum. Group V3 specimens were sintered to 1090° C., held for 30 minutes without any vacuum. Group V4 specimens were sintered to 1200° C., held for 5 minutes without any vacuum. Group V5 specimens were sintered to 1200° C., held for 5 minutes with 5 minutes of vacuum.

VITA VM 9 was especially designed as a high fusing, fine structure feldspar ceramic for zirconia substructures partially stabilized with yttrium with a coefficient of thermal expansion (CTE) approximately $10.5 \times 10^{-6}$ $K^{-1}$. The CTE is adjusted to suit zirconia materials, thereby promising strong bonding and reliable results. This 3D-Master and VITA Classical shaded porcelain is compatible with VITA's In-Ceram YZ Cubes for CEREC® and many of today's zirconia substructure materials.

Specimens in groups G1-G6 used VITA In-Ceram ZR as the adhesive. Group G1 specimens were sintered to 1050° C., held for 10 min without any vacuum. This group had 4 subgroups: (i) G1A, bars used were as-sintered, (ii) G1B, bars were abrasively blasted, (iii) G1C, a weight of 104 g was placed on the specimens while they were sintered, and (iv) G1D, the specimens were abrasively blasted and a weight of 104 g was placed on the specimens. Groups G2-G7 specimens did not have weight or surface treatment. Group G2 specimens were sintered to 1000° C., held for 5 minutes with 5-minute vacuum. G3 specimens were sintered to 1050° C., held for 5 minutes with 5 minutes of vacuum. G4 specimens were sintered to 1100° C., held for 5 minutes with 5 minutes of vacuum. G5 specimens were sintered to 1150° C., held for 5 minutes with 5 minutes of vacuum. G6 specimens were sintered to 1200° C., held for 5 minutes without any vacuum. G7 specimens were sintered to 1200° C., held for 5 minutes with 5 minutes of vacuum.

Group F specimens used infusion glass mixed with 10% $B_2O_3$. The materials were mixed by grinding with a mortar and pestle for 10 minutes, then sintered in a high temperature tube furnace (Thermolyne #59300) at 1500° C. for 60 minutes. The final shape of the mixture when it cooled was a solid small ball. A hammer mill was used to crush the ball and a mortar and pestle was used to grind it into frit. Group F specimens were divided into 6 subgroups. All specimens had the ground frit powder mixed with de-ionized water and were sintered at different temperatures for 5 minutes. Group F1 specimens were sintered to 900° C., Group F2 specimens were sintered to 950° C., Group F3 specimens were sintered to 1000° C., Group F4 specimens were sintered to 1050° C., Group F5 specimens were sintered to 1200° C., and Group F6 specimens were sintered to 1200° C., and had 5 minutes of vacuum.

Group AG specimens were fused with a mixture of infusion glass and $Al_2O_3$ (30 wt % infusion glass, 70 wt % $Al_2O_3$). The specimens were divided into two subgroups: AG-1, where the bars had neither surface treatment nor coating and AG-2, where the bars were coated with colloidal silica (LUDOX CL-P) before fusing. The mixture of infusion glass and $Al_2O_3$ was mixed with de-ionized water in both subgroups and the specimens were sintered to 1050° C. and held for 5 min without any vacuum.

Group CZ specimens used colloidal zirconia (a liquid suspension of zirconia): three drops of the colloid were applied on each bars and then placed in a Thermolyne #48000 furnace at a temperature of 50° C. for 24 hours. Later, they were sintered to 1050° C. and held for 5 min without any vacuum.

Group MZ specimens used mullite zirconia (36.0% $ZrO_2$, 45.8% $Al_2O_3$, and 17.5% $SiO_2$), which was mixed with deionized water. The specimens were sintered to 1050° C. and held for 5 minutes without any vacuum.

Example 4 Finishing Procedures

Specimens were finished with a Buehler EcoMet® 250 Grinder-Polisher. Ultraprep diamond grinding disc (Buehler 15 µm, Buehler Ltd) was used at a speed of 20 rpm, this was done to remove excess materials left after bonding or sintering.

Example 5 Optical Microscopy

The failure modes of the specimens were evaluated using optical microscopy at various magnifications.

Optical micrographs of randomly selected fractured specimens from each group were taken. Micrographs of the cross-sections of tested specimens were obtained by mounting the bars of each specimen opposite to each other embedded in an epoxy clear acrylic resin-filled silicon rubber. The specimens were sectioned by Buehler Isomet 2000 precision saw. Finishing and polishing of the specimens was done using a variable-speed grinder-polisher machine (Ecomet 3, Buehler Ltd). Diamond grinding and polishing discs (Buehler ultra-prep 70-µm, 45-µm, 15-µm, 6-µm and finally 1-µm), were used at 50 rpm. The optical micrographs of the debonded surfaces of the bars were obtained at magnifications of 5×, 10×, 20× and 50× to determine whether the mode of failure was cohesive or/and adhesive, and to determine the thickness of the bonding material and whether any of it was incorporated within the $ZrO_2$ bars.

Example 6 Flexural Load at Break

The flexure load at break of the specimens was determined using a 3-point bending test with an Instron Model #5566 universal testing machine (1000 Newtons load cell and a crosshead speed of 0.5 mm/min). The specimens were marked with a pencil at the areas where they contacted the rollers of the fixture. The laboratory temperature was around 25° C.

Bluehill 2 software was used to obtain the mean values of failure load. Group RA-GA was considered as the control group. The results for group R and group M specimens are shown in Tables 1 and 2, respectively. Abrasive blasting and coating with Monobond positively affected the bonding between the bars.

TABLE 1

Mean failure loads for group R specimens

| Subgroups | N | Failure Loads | SD | COV % |
|---|---|---|---|---|
| RA-Ga | 4 | 45.87 | 6.22 | 13.56 |
| RSb-Ga | 4 | 64.38 | 20.47 | 31.79 |
| RA-GA-m | 5 | 123.22 | 17.24 | 13.99 |
| RA-GB | 4 | 60.32 | 12.94 | 21.45 |
| RSb-Gb | 4 | 79.4 | 16.51 | 20.79 |

TABLE 2

Mean failure loads for group M specimens

| Subgroups | N | Failure Loads | SD | COV % |
|---|---|---|---|---|
| MA-m | 10 | 136.06 | 26.33 | 19.35 |
| MSb-m | 10 | 172.33 | 29.36 | 17.04 |
| MA-nm | 5 | 34.69 | 21.18 | 61.05 |
| MSb-nm | 5 | 48.58 | 14.66 | 30.18 |

The results for group V specimens are shown in Table 3. The specimens had larger failure loads than specimens in groups R and M when the specimens was sintered to 1200° C. Specimens in subgroup V5 experienced a 5-minute vacuum and showed largest failure load in Group V.

TABLE 3

Mean failure loads for group V specimens

| Subgroups | N | Failure Loads | SD | COV % |
|---|---|---|---|---|
| V1 - 950° C. | 7 | 52.7 | 12.68 | 24.06 |
| V2 - 980° C. | 5 | 74.03 | 24.99 | 33.76 |
| V3 - 1090° C. | 5 | 94.13 | 32.97 | 35.03 |
| V4 - 1200° C. | 5 | 190.73 | 23.47 | 12.3 |
| V5v - 1200° C. | 10 | 228.97 | 17.72 | 7.74 |

Figure 5:
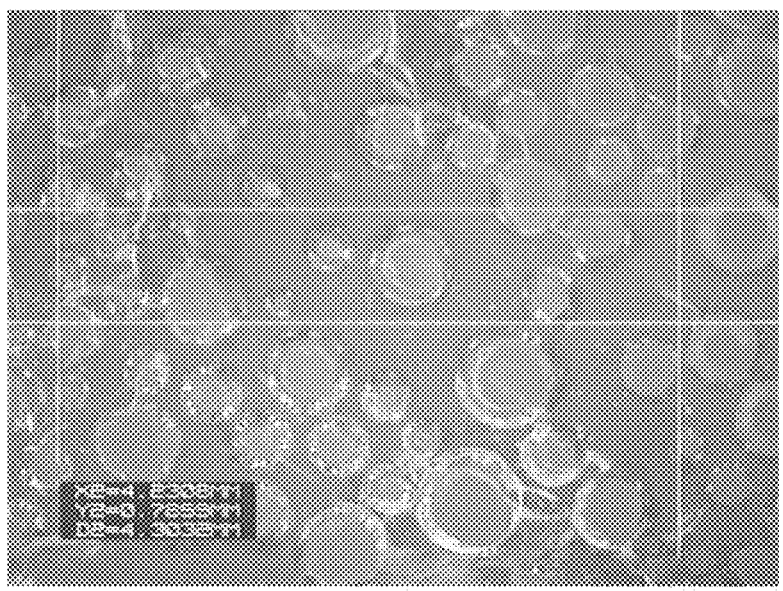
FIG. 5 is an optical micrograph (10× magnification) of a bar from a group G1A specimen which debonded.
Figure 6:
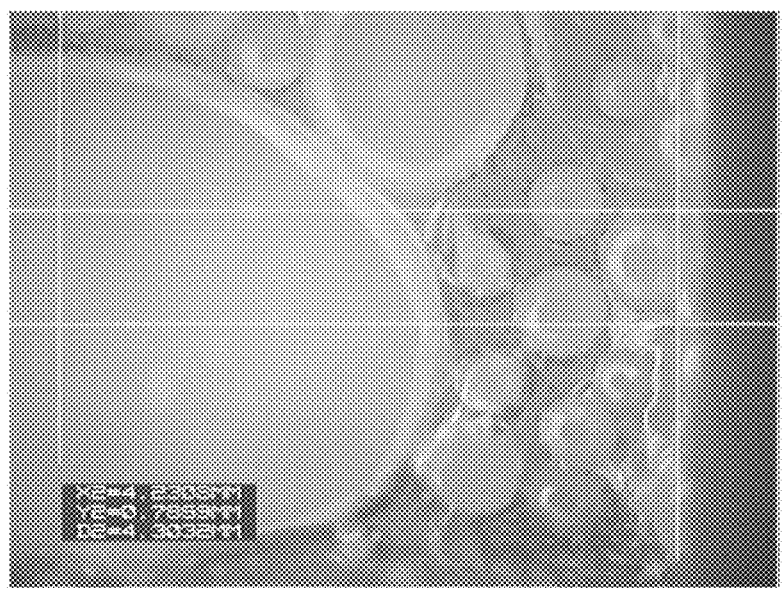
FIG. 6 is an optical micrograph (10× magnification) of the surface of a bar from another group G1A specimen which debonded.

The results for group G1 specimens are shown in Table 4. As-sintered specimens (G1A) had larger failure loads than the abrasively blasted specimens and specimens from other subgroups which were sintered with a weight of 104 g. Micrographs (taken with optical microscope at 10× magnification) of two specimens from subgroup G1A are shown in FIGS. 5 and 6. FIG. 5 relates to a specimen with the highest failure load in Group G1A and had bubbles of small size within the infusion glass. The other specimen with the lowest failure load in group G1A had larger bubbles within the infusion glass (FIG. 6).

TABLE 4

Mean failure loads for group G1 specimens

| G1 1050° C. Subgroups | N | Newtons | SD | COV % |
|---|---|---|---|---|
| G1A | 5 | 146.04 | 55.22 | 37.81 |
| G1Sb | 3 | 81.46 | 23.14 | 28.41 |

TABLE 4-continued

Mean failure loads for group G1 specimens

| G1 1050° C. Subgroups | N | Newtons | SD | COV % |
|---|---|---|---|---|
| G1W | 3 | 53.28 | 27.02 | 50.71 |
| G1SbW | 3 | 84.99 | 5.06 | 5.95 |

Figure 7:
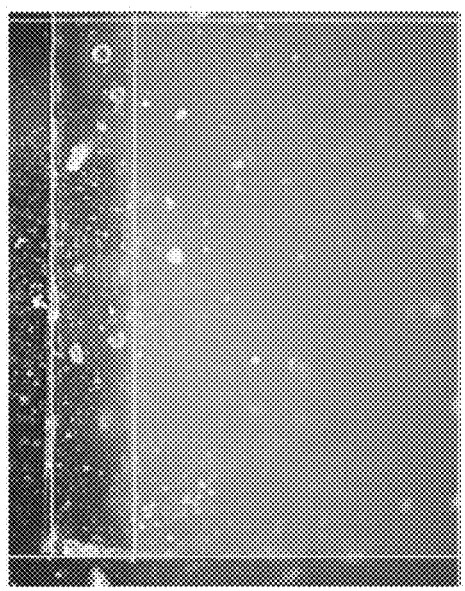
FIG. 7 is an optical micrograph (20× magnification) of the cross-section of as-sintered group G1A specimen.
Figure 8:
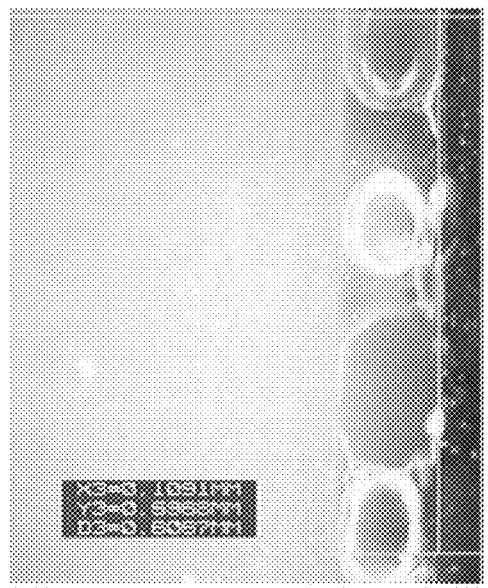
FIG. 8 is an optical micrograph (20× magnification) of the cross-section of an abrasively blasted group G1Sb specimen.

FIGS. 7 and 8 are optical micrographs (20× magnification) of the cross sections of an as-sintered (G1A) specimen and an abrasively blasted (G1Sb) specimen, respectively. The G1A specimen had smaller bubbles within the glass with a failure load of 146.04 N, while the failure load of the G1Sb specimen was 81.46 N and had larger bubbles within the glass.

Figure 9:
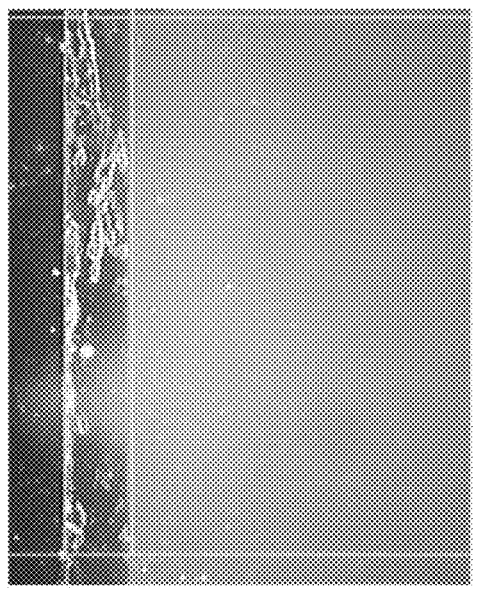
FIG. 9 is an optical micrograph (20× magnification) of the cross-section of a group G1W specimen which had a 104-g weight placed on the specimen while being sintered.
Figure 10:
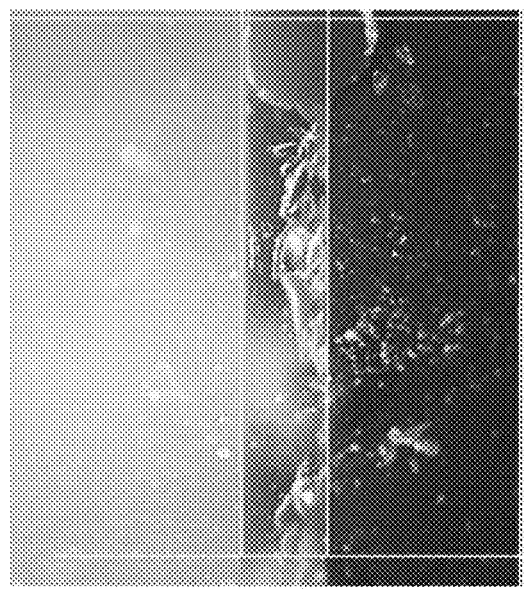
FIG. 10 is an optical micrograph (20× magnification) of the cross-section of an abrasively blasted group G1SbW specimen which had a 104-g weight placed on the specimen while being sintered.

FIGS. 9 and 10 are optical micrographs (20× magnification) of the cross sections of a specimen (G1W) that had a 104-g weight placed on it while being sintered and another specimen (G1SbW) which had the abrasively blasted bars and the 104-g weight placed on it during sintering, respectively. The G1W specimen had cracks within the glass, and G1Sb specimen had large bubbles with cracks within the glass.

Group G specimens had the highest values of failure load in this study, with group G7 specimens having the largest failure load. All specimens were pre-heated to 600° C., heated at a rate of 80° C./min to the end temperature (e.g. 1000° C. for group G2 specimens), which was sustained for 5 minutes and then treated to 5 minutes of vacuum, except for group G6 specimens (without vacuum). The results are show in Table 5.

TABLE 5

Mean failure loads for specimens in groups G2-G7

| Subgroups | N | Failure load | SD | COV % |
|---|---|---|---|---|
| G2 1000° C. | 10 | 85.53 | 14.39 | 16.82 |
| G3 1050° C. | 10 | 213.94 | 68.08 | 31.82 |
| G4 1100° C. | 10 | 293.75 | 82.91 | 28.22 |
| G5 1150° C. | 10 | 363.71 | 62.41 | 17.16 |
| G6 1200° C. | 6 | 369.07 | 56.06 | 15.19 |
| G7 1200° C. | 10 | 460.32 | 86.07 | 18.7 |

Figure 11:
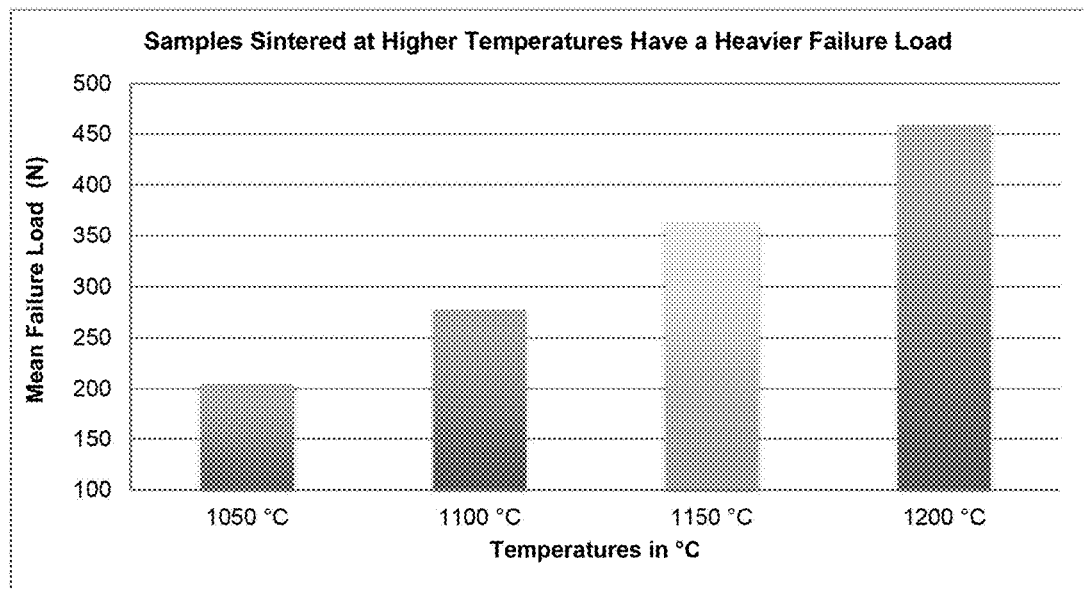
FIG. 11 shows the mean values of failure load for specimens in groups G2, G3, G4, G5, and G7.
Figure 12:
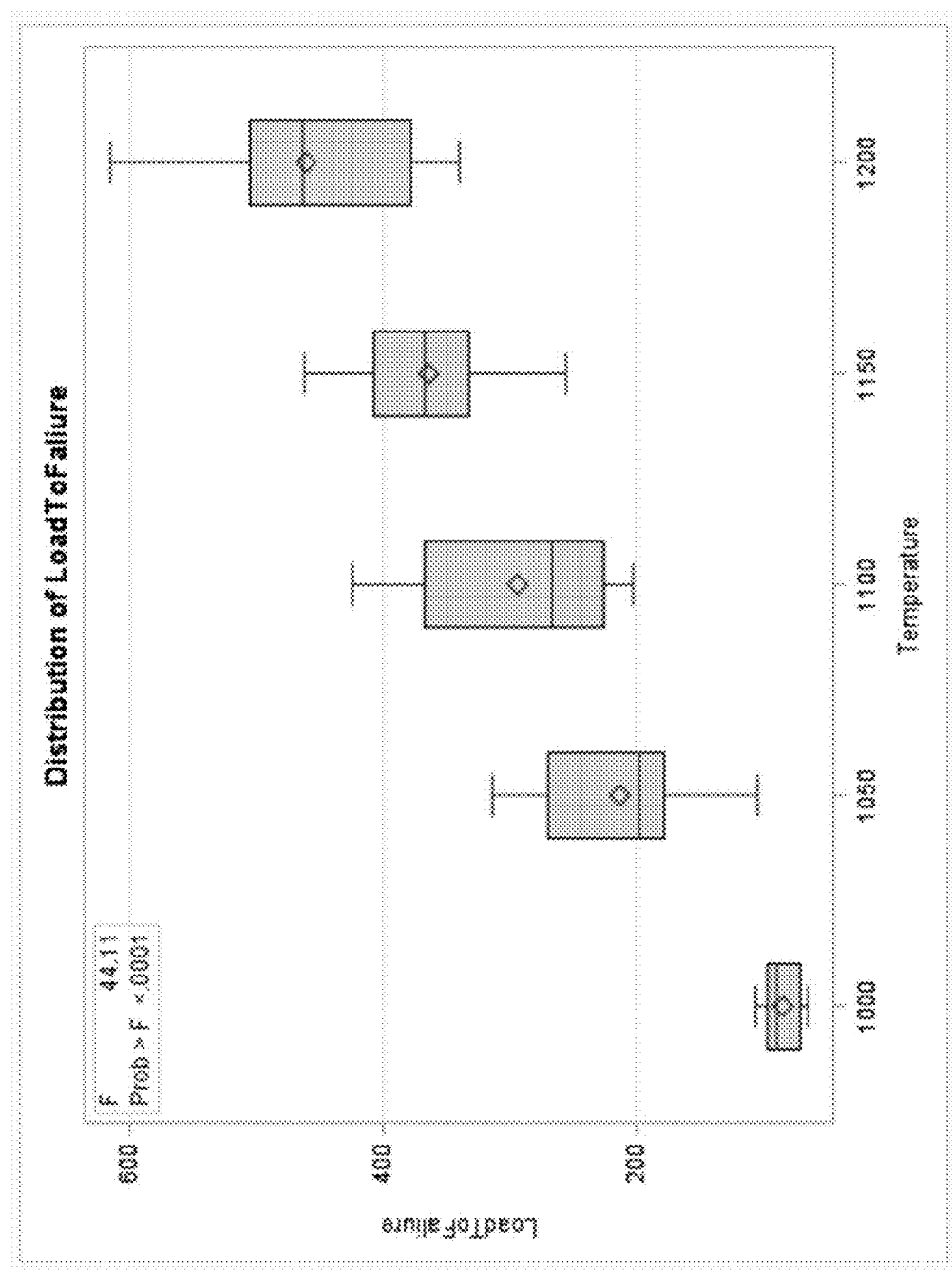
FIG. 12 shows the mean values and standard deviations of failure load for specimens in groups G2, G3, G4, G5, and G7.

The mean values of failure load of specimens of subgroups G2, G3, G4, G5, and G7 are shown in FIG. 11, and the mean values and standard deviations of failure load are shown in FIG. 12. The values 85.53±14.39 N (G2), 213.94±68.08 N (G3), 293.75±82.91 N (G4), 363.71±62.41 N (G5), and 460.32±86.07 N (G7).

Based on statistical analysis, there is significant evidence at α=0.05 to show that there is a difference in the values of the failure load between the groups. Group 1 represents G2 specimens, group 2 represents G3 specimens, group 3 represents G4 specimens, group 4 represents G5 specimens, and group 5 represents G7 specimens. Further post hoc tests (analysis of variance (ANOVA) with Tukey multiple comparison statistics) revealed that:

1. Group 2 is statistically significantly different from group 1 with p value=0.0011.

2. Group 3 is not statistically significantly different from group 2 with p value=0.0835.

3. Group 4 is not statistically significantly different from group 3 with p value=0.1649.
4. Group 5 is statistically significantly different from group 4 with p value=0.0218.

The results are summarized in Table 6.

TABLE 6

P-values between each group

| i | 1 | 2 | 3 | 4 | 5 |
|---|---|---|---|---|---|
| 1 |   | 0.0011 | <.0001 | <.0001 | <.0001 |
| 2 | 0.0011 |   | 0.0835 | 0.0001 | <.0001 |
| 3 | <.0001 | 0.0835 |   | 0.1649 | <.0001 |
| 4 | <.0001 | 0.0001 | 0.1649 |   | 0.0218 |
| 5 | <.0001 | <.0001 | <.0001 | 0.0218 |   |

Table 7 shows the mean values of failure load for specimens in subgroups F1-F6. All specimens experienced a holding time of 5 minutes at the end temperature. Only the specimens in subgroup F6 had 5 of minutes vacuum during sintering and had an average failure load of 214.52 N.

TABLE 7

Mean failure loads for group F specimens

| Subgroups | N | Failure load | SD | COV % |
|---|---|---|---|---|
| F1 900° C. | 3 | 49.12 | 12.68 | 25.81 |
| F2 950° C. | 3 | 74.08 | 24.99 | 33.73 |
| F3 1000° C. | 3 | 80.17 | 32.97 | 41.12 |
| F4 1050° C. | 3 | 82.4 | 23.47 | 28.48 |
| F5 1200° C. | 6 | 194.12 | 17.72 | 9.12 |
| F6 1200° C. | 3 | 214.52 | 23.47 | 10.94 |

The invention claimed is:

1. A method for forming a fixed partial denture, comprising:
    milling a porous ceramic block into a shape of a series of teeth thereby forming a pre-sintered framework structure comprising:
        a plurality of retainers; and
        a pontic located between and connected to adjacent retainers via a connector;
    sintering the pre-sintered framework structure thereby forming an initial sintered framework structure;
    separating the initial sintered framework structure at the connector thereby providing a plurality of sintered retainers and a sintered pontic;
    seating each sintered retainer and aligning the sintered pontic on a respective tooth abutment within a patient's mouth or on a dental model so as to provide an accurate fit; and
    rejoining each sintered retainer to the sintered pontic thereby forming a final framework structure and sintering to form the fixed partial denture,
    wherein the fixed partial denture comprises:
    at least 90% $ZrO_2$ by weight;
    at least 3% $Y_2O_3$ by weight;
    at least 1% $HfO_2$ by weight;
    no more than 0.1% $Al_2O_3$ by weight;
    no more than 0.1% $SiO_2$ by weight; and
    no more than 0.1% $Na_2O$ by weight of the fixed partial denture.

2. The method of claim 1, wherein the porous ceramic block comprises porous pre-sintered zirconia.

3. The method of claim 2, wherein the porous ceramic block further comprises yttrium oxide.

4. The method of claim 1, wherein at least one of the pre-sintered framework structure and the final framework structure is sintered in a pressure ranging from 1-50 mbar.

5. The method of claim 1, wherein at least one of the pre-sintered framework structure and the final framework structure is sintered at a temperature ranging from 900° C. to 1500° C.

6. The method of claim 5, wherein at least one of the pre-sintered framework structure and the final framework structure is sintered at a temperature ranging from 1000° C. to 1200° C.

7. The method of claim 1, wherein at least one of the pre-sintered framework structure and the final framework structure is sintered for a period ranging from 1-60 minutes.

8. The method of claim 7, wherein at least one of the pre-sintered framework structure and the final framework structure is sintered for a period ranging from 5-10 minutes.

9. The method of claim 1, wherein the initial sintered framework structure is separated by ultrasonic vibration-assisted machining, laser-assisted machining, or thermal-assisted machining.

10. The method of claim 9, wherein the initial sintered framework structure is separated by laser-assisted machining.

11. The method of claim 1, wherein the initial sintered framework structure is separated by ultrasonic vibration-assisted machining, laser-assisted machining, or thermal-assisted machining, and the method further comprises separating the initial sintered framework structure with a machining tool heated to a temperature up to 500° C.

12. The method of claim 1, wherein the accurate fit is provided by seating each sintered retainer and aligning the sintered pontic on the respective tooth abutment within the patient's mouth.

13. The method of claim 1, wherein the accurate fit is provided by seating each sintered retainer and aligning the sintered pontic on the respective tooth abutment of the dental model.

14. The method of claim 1, wherein each sintered retainer is rejoined to the sintered pontic by applying a glass therebetween.

15. The method of claim 14, wherein the glass is in the form of a paste.

16. A fixed partial denture, comprising:
    at least 90% $ZrO_2$ by weight;
    at least 3% $Y_2O_3$ by weight;
    at least 1% $HfO_2$ by weight;
    no more than 0.1% $Al_2O_3$ by weight;
    no more than 0.1% $SiO_2$ by weight; and
    no more than 0.1% $Na_2O$ by weight of the fixed partial denture;
    wherein the fixed partial denture is in the form of a plurality of retainers and a pontic located between and connected to adjacent retainers via a connector and which does not have a porcelain veneer.

17. The fixed partial denture of claim 16, comprising:
    91-94% $ZrO_2$ by weight;
    4-6% $Y_2O_3$ by weight;
    2-4% $HfO_2$ by weight;
    no more than 0.1% $Al_2O_3$ by weight;

no more than 0.1% $SiO_2$ by weight; and
no more than 0.1% $Na_2O$ by weight of the fixed partial denture.

18. The fixed partial denture of claim 16, which has a failure load in a range of 200-700 N.

* * * * *